United States Patent
DiVito

(10) Patent No.: US 9,119,909 B1
(45) Date of Patent: Sep. 1, 2015

(54) IV HOLDER

(71) Applicant: Brian P. DiVito, St. Petersburg, FL (US)

(72) Inventor: Brian P. DiVito, St. Petersburg, FL (US)

( * ) Notice: Subject to any disclaimer, the term of this patent is extended or adjusted under 35 U.S.C. 154(b) by 0 days.

(21) Appl. No.: 14/182,013

(22) Filed: Feb. 17, 2014

(51) Int. Cl.
 *F16M 11/08* (2006.01)
 *A61M 5/14* (2006.01)
 *F16M 11/22* (2006.01)
 *F16M 11/42* (2006.01)

(52) U.S. Cl.
 CPC ............. *A61M 5/1417* (2013.01); *F16M 11/08* (2013.01); *F16M 11/22* (2013.01); *F16M 11/42* (2013.01)

(58) Field of Classification Search
 CPC .... A61M 5/1417; F16M 11/08; F16M 11/22; F16M 11/42
 See application file for complete search history.

(56) References Cited

U.S. PATENT DOCUMENTS

| 3,043,546 | A | * | 7/1962 | Reich ............................ 248/215 |
| 3,559,935 | A | * | 2/1971 | Gardner ..................... 248/125.8 |
| 4,143,652 | A | * | 3/1979 | Meier et al. ................... 600/203 |
| 5,188,323 | A | * | 2/1993 | David ........................... 248/158 |
| 5,273,402 | A | * | 12/1993 | Maury ......................... 416/246 |
| 6,834,837 | B2 | * | 12/2004 | Schilt et al. ................ 248/284.1 |
| 2007/0259555 | A1 | * | 11/2007 | Conforti ....................... 439/369 |
| 2011/0303805 | A1 | * | 12/2011 | Lau et al. ................... 248/125.8 |
| 2013/0228997 | A1 | * | 9/2013 | Fukuhara et al. .......... 280/304.1 |

* cited by examiner

*Primary Examiner* — Jeanette E Chapman
(74) *Attorney, Agent, or Firm* — Larson & Larson, P.A.; Frank Liebenow; Patrick Reid

(57) ABSTRACT

An IV holder includes a base for supporting the IV holder on a floor. A first end of a post extends from the base and a distal second end area of the post has an IV bag hook. The IV bag hook is positioned substantially over a center of gravity of the IV holder when the base is positioned on the floor. The post has an offset area so that the post doesn't interfere with an IV bag suspended from the IV bag hook.

18 Claims, 3 Drawing Sheets

IV HOLDER

FIELD

This invention relates to the field of holders or stands and more particularly to a holder/stand for supporting an bag holding fluids such as an Intravenous (IV) bag.

BACKGROUND

An intravenous bag or IV bag typically supplies fluid to a patient in a slow, controlled administration through a needle injected into the patient's vein, typically a vein in the patient's wrist, arm, or leg. There are many types of fluids that are delivered from an IV bag, through a needle and directly into a patient's vein including saline solution, blood products, medication, etc. The fluid is typically not under any external pressure and feeds through the needle by force of gravity, hence the IV bag needs to be positioned at a location above the patient to provide flow of the fluid from the IV bag into the patient's vein.

Because the fluid from the IV bag is administered over a long period of time, the patient must be in vicinity of the IV bag, at least limited by the practical length of a tube that connects the IV bag to the needle that is inserted in the patient's vein. Being such, the patient is virtually tethered to the IV bag.

To provide the patient with some degree of mobility, often the IV bag is supported by a portable IV holder, often having wheels. In such, the patient is relatively free to move about to exercise, use the bathroom, etc. The patient pushes/pulls the IV holder, and hence the IV bag, along with them as they make their way to their desired destination. Such is often witnessed in many hospitals.

As will be shown, the typical prior IV holder consisted of a substantially linear shaft with a base and wheels at one end and an arm extending from a distal end to which the IV bag is attached. Although often adjustable in height, the IV bag is typically supported anywhere from six to eight feet off of the floor. Being that a full IV bag typically contains a pint of fluid and the fluid has a specific gravity similar to that of water, a full IV bag typically weights around one pound. Being that the IV bag is positioned on an arm, the weight of the IV bag and the distance from the substantially linear shaft creates an imbalance to the prior IV holder, the longer the arm and the heavier the IV bag, the greater the imbalance. As the patient walks to their destination, any obstruction such as a change in floor surfaces, minor bumps, etc., will perturb the prior IV holder, possibly leading to the IV holder, and hence, the IV bag falling, which possibly leads to bursting of the IV bag, damaging furniture or equipment from the IV holder hitting such, bodily injury, etc.

What is needed is an IV holder that will reduce imbalances and, therefore, reduce the potential of tipping.

SUMMARY

In one embodiment, an IV holder is disclosed including a base for supporting the IV holder on a floor. A first end of a post extends from the base and a distal second end area of the post has an IV bag hook. The IV bag hook is positioned substantially over a center of gravity of the IV holder when the base is positioned on the floor. The post has an offset area so that the post doesn't interfere with an IV bag suspended from the IV bag hook.

In another embodiment, an IV holder is disclosed including a base that has a plurality of wheels interfaced to a first side; the wheels for supporting the IV holder on a floor. The IV holder also includes a post (generally horizontal when the base is positioned on the floor). A first end of the post extends from the second side of the base (opposite from the first side of the base), a distal end area of the post is connected to an IV bag hook. The post has an offset area between the first end and the second end such that the IV bag hook is positioned over a center of the base. When an IV bag is attached to the IV bag hook, the IV bag is positioned in the offset area so that the post doesn't interfere with the IV bag.

In another embodiment, an IV holder is disclosed including a base that has a plurality of wheels interfaced to a first side for supporting the IV holder on a floor and allowing movement in a generally horizontal plane. A device for supporting an IV bag hook is interfaced to the base such that the IV bag hook is positioned substantially over a center of the base. The device for supporting is, for example, a post that has an offset area so that an IV bag held by the IV bag hook is not interfered with by the post.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figures 1, 2:
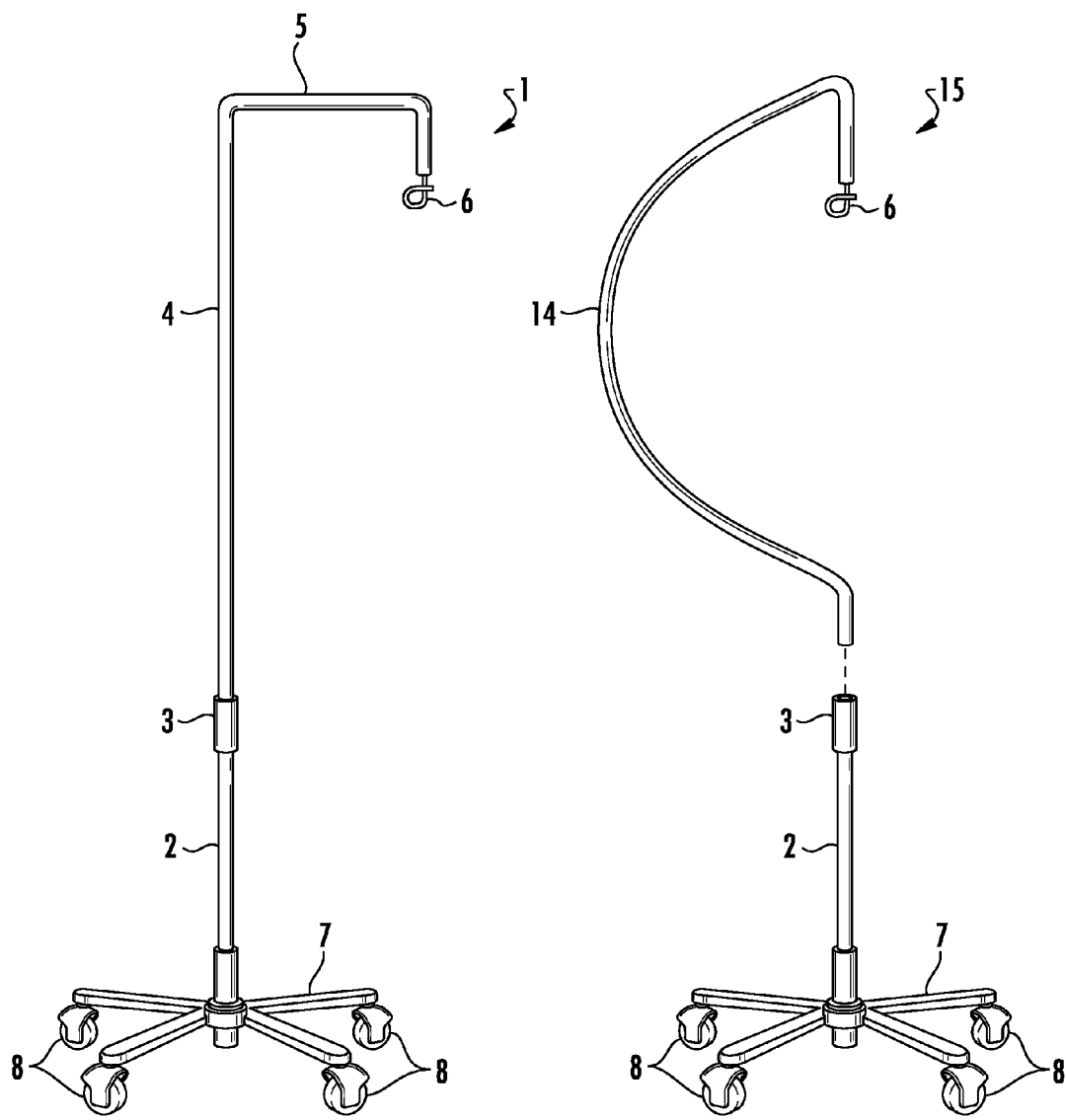
FIG. 1 illustrates a perspective view of an IV holder of the prior art.
FIG. 2 illustrates a perspective view of a new IV holder.

Reference will now be made in detail to the presently preferred embodiments of the invention, examples of which are illustrated in the accompanying drawings. Throughout the following detailed description, the same reference numerals refer to the same elements in all figures.

Referring to FIG. 1, a perspective view of an IV holder 1 of the prior art id shown. A typical IV holder 1 has a base 7 with wheels 8 and a substantially linear post 2/3/4, shown in this example comprising of a lower post 2, a telescoping adjustment lock 3, and an upper post 4. In this configuration, the height of the IV bag 52 (See FIGS. 5-7) is adjustable to some degree. The top end of the upper post 4 extends outwardly as an arm 5 and the arm 5 terminates in an IV bag hook 6 as known in the industry.

Being that IV bags 52 are relatively heavy, the IV holder 1 of the prior art is held off balance since the weight of the IV bag 52 is held distal from the center of gravity of the overall IV holder 1. The IV bag 52 exerts an angular force proportional to the height of the IV post 2/3/4, the length of the arm 5, and the weight of the IV bag 52.

To improve mobility, the IV holder 1 of the prior art is typically made of a light weight material such as aluminum or a light gauge steel, and has wheels 8. As such, the IV holder 1 of the prior art typically has sufficient mass so as to counteract the above described angular force, remaining stable while the IV holder 1 of the prior art stands on a substantially flat, horizontal surface, but instability occurs during many situations. Instability occurs when moving the IV pole 1 of the prior art, especially when impediments to movement are encountered such as surface changes (e.g. linoleum to carpet), door thresholds, debris on the floor, ramps, etc. When a patient traverses a floor area, such impediments often result in loss of control of the IV holder 1 of the prior art, leading to property damage and potentially bodily harm to the patient and others.

Figures 3, 4:
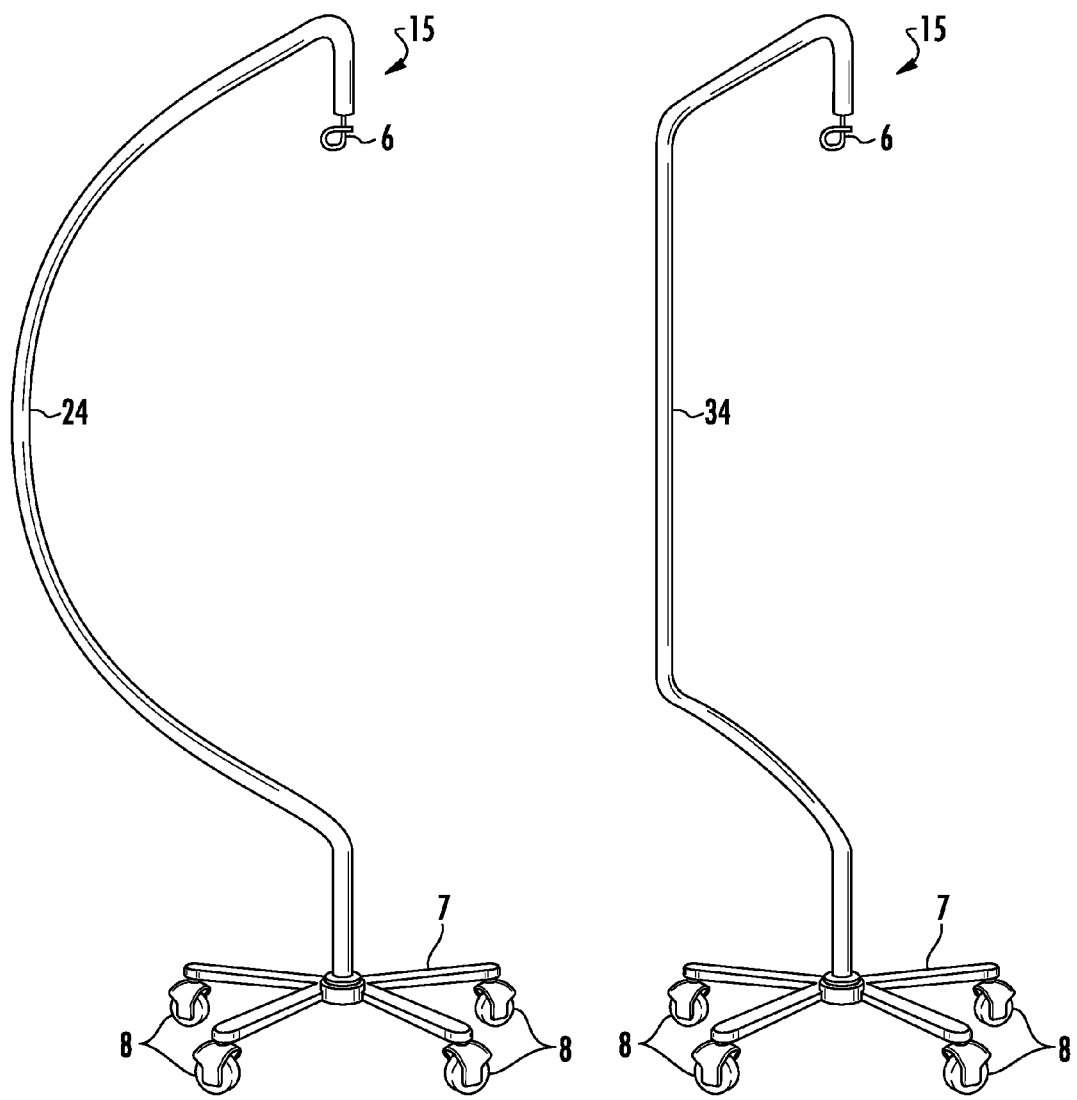
FIG. 3 illustrates a perspective view of the new IV holder.
FIG. 4 illustrates a perspective view of the new IV holder.

Referring to FIGS. 2, 3 and 4, perspective views of a new IV holder are shown. To improve stability, of the IV holder 15 is balanced, reducing or eliminating the angular offset force described in the prior art. In the IV holders 15, the IV bag 52 is suspended in a position that provides less angular force and, therefore, the IV holder 15 is less likely to tip over when encountering impediments as described above. To accomplish such balance, the mass of the IV bag 52 is suspended in a location that is closer to the center of the base 7 and wheels 8, roughly the center of gravity of the IV holder 15. As shown in FIG. 2, the same base 7, wheels 8, lower post 2 and lock 3 are retrofitted with a new upper post/arm 14 which curves outwardly from the center of the base 7 so that the IV bag hook 6 is positioned roughly central to the base 7 and wheels 8, at a location that approximately balances the IV holder 15. In this way, the mass of the IV bag 52, hung from the IV bag hook 6 will not place the IV holder 15 off balance, thereby reducing the potential for tipping. Note that it is anticipated that the mass of the upper post/arm 14 will provide a slight angular force (tipping force) in one direction (e.g. towards the left as shown in FIG. 2) and, therefore, the IV bag hook 6 is anticipated to be positioned just past center (e.g. towards the right as shown in FIG. 2) to balance the slight angular force of the upper post/arm 14.

Throughout the description, the terms "substantially center," "just past center," "roughly central to the base 7," and "approximately balances" are not exact terms because the exact mass of the IV bag and contents of the IV bag 52 are not constant. Therefore, for design purposes, if the location of the IV bag hook 6 is exactly center to the base 7, then the IV holder 15 will be slightly off balance when the IV bag 52 is full due to the mass of the outwardly swinging portion of the post 14/24/34. As the IV bag 52 empties, the IV holder 15 will grow further off balance since the mass of the fluid that was in the IV bag 52 will no longer counteract the mass of the outwardly swinging portion of the post 14/24/34. On the other hand, if the location of the IV bag hook 6 is offset slightly opposite of the outwardly swinging portion of the post 14/24/34, the IV holder will be slightly off balance to the side of the IV bag 52 when the IV bag 52 is full, then the IV holder 15 will be balanced when the IV bag 52 is half empty, and then the IV holder 15 will be slightly off balance to the side opposite of the IV bag 52 when the IV bag 52 is empty.

Besides providing improved stability, the IV holder 15 as shown in FIGS. 2, 3, and 4 also provides an improved place to grasp, that being the post/arm 14. In the prior art IV holder 1, the patient had to extend an arm further to grasp and had to maneuver around the base 7 and wheels 8. In the IV holder 15 as shown in FIGS. 2, 3, and 4, the patient grasps the post/arm 14 and is thereby automatically distant from the base 7 and wheels 8, reducing interference with walking. Note also that the post/arm 14 provides better protection to the IV bag 52 as the patient maneuvers. For example, if the IV holder 1 of the prior art was pushed up against a wall, the IV bag 52 would hit the wall, while if the IV holder 15 shown in FIGS. 2, 3, and 4 is pushed up against a wall, the IV bag 52 being roughly centered over the base 7 and wheels 8 would not hit the wall.

In FIG. 3, an alternate design of the IV holder 15 is shown in which the post/arm 24 is one integrated section (e.g., does not telescope). Although the curvature of the post/arm 14 and post/arm 24 are shown having an approximately parabolic curve which is known to have better structural characteristics than, for example, an arc, any shape of post/arm is anticipated including an arc, squared edges, or that shown in FIG. 4 having a flattened post/arm 34. There is no limitation on the shape of the post/arm 14/24/34 and those shown are examples. Any shape of post/arm 14/24/34 is anticipated as long as that shape of post/arm 14/24/34 positions the IV bag hook 6 at a location that provides balance to the IV holder 15 when an IV bag 52 is attached to the IV bag hook 6.

Figure 5:
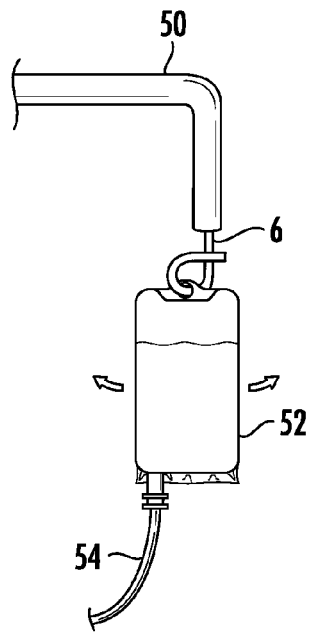
FIG. 5 illustrates a perspective view of an IV bag hanger as used with the IV holder of the prior art.

Referring to FIG. 5, a perspective view of an IV bag hanger of the prior art is shown. In the prior art, the IV bag 52 is looped onto an IV bag hook 6 as shown, with an IV tube 54 typically extending from the lowest location on the IB bag 52. The hook is directly connected to an arm 50 (similar to arm 5, or any arm 50). As the IV pole (e.g. IV pole 2/3/4) is moved, the IV bag 52 swings on the IV hook 6, creating further instability to the IV holders 1 of the prior art due to the force exerted by the moving mass of the IV bag 52.

Figure 6:
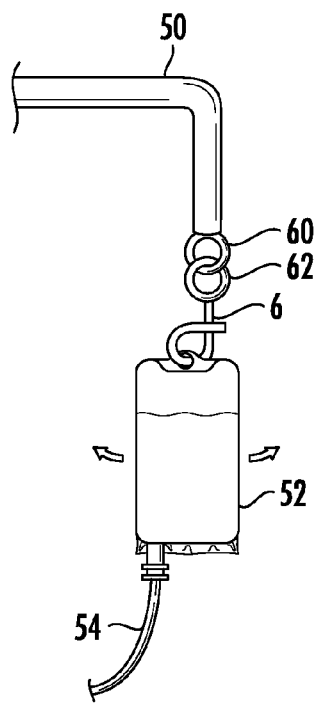
FIG. 6 illustrates a perspective view of a new IV bag hanger as used with the new or any IV holder.
Figure 7:
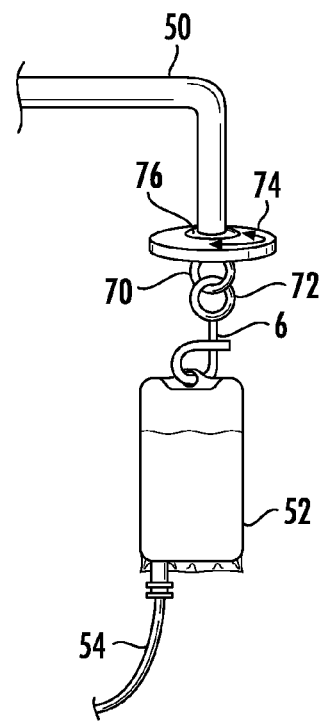
FIG. 7 illustrates a perspective view of a new IV bag hanger as used with the new or any IV holder.

Referring to FIGS. 6 and 7, perspective views of a new IV bag hanger as used with the new or any IV holder are shown. In both FIGS. 6 and 7, the IV hook 6 is interfaced to the arm 50 (e.g. any arm 5, 14, 24, 34) by a damper 60/62/70/72. In FIG. 6, the damper consists of intertwined circular links. A first circular link 60 is affixed to the arm 50 and a second circular link 62 is affixed to the IV hook. In FIG. 7, the damper consists of a first circular link 70 that is affixed to a rotating member 74 and a second circular link 72 that is affixed to the IV hook 6. The dampers 60/62/70/72 dampen swinging motion of the IV bag 52 as shown by arrows in FIG. 6.

To further improve ease of use as well as safety, in FIG. 7, a first rotating member 76 of a bearing 74/76 (shown as a disc, but there are no shape limitations on member 74) is connected to the arm 50 and a second rotating member 74 of the bearing 74/76 is connected to the IV hook 6 (e.g., by circular links 70/72), allowing the IV bag 52 to rotate as depicted by the arrows shown in FIG. 7. In some embodiments, the rotating member 74 freely rotates with respect to the arm 50 while in other embodiments, rotation of the rotating member 74 is limited to less than 360 degrees so as to not twist the IV tube 54.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. An IV holder comprising:
   a base, the base for supporting the IV holder on a floor;
   a post, a first end of the post extending from the base and a distal second end area of the post having an IV bag hook; and
   means for allowing rotation of an IV bag that includes a bearing, a first rotating member of the bearing interfaced to the distal second end area of the post and a second rotating member of the bearing interfaced to the IV bag hook;

whereas the IV bag hook is positioned substantially over a center of gravity of the IV holder when the base is positioned on the floor.

2. The IV holder of claim 1, wherein the post includes a curved section, the curved section jutting outwardly from the center of gravity of the IV holder.

3. The IV holder of claim 2, wherein the IV bag hook is positioned such that an IV bag hanging from the IV bag hook is held in an area between endpoints of the curved section, thereby, the IV bag hangs centrally over the base.

4. The IV holder of claim 1, wherein the base as a first side and an opposing second side, the post extending from the first side, whereas the base further comprises a plurality of wheels, the plurality of wheels interfaced to the second side of the base.

5. The IV holder of claim 1, further comprising means for damping movement of an IV bag that hangs from the IV bag hook.

6. The IV holder of claim 5, wherein the means for damping comprises a pair of intertwined circular links, a first circular link of the pair of intertwined circular links interfaced to the distal second end area of the post and a second circular link of the pair of intertwined circular links interfaced to the IV bag hook.

7. The IV holder of claim 1, wherein the means for allowing rotation of the IV bag that hangs from the IV bag hook.

8. An IV holder comprising:
 a base, the base having a plurality of wheels interfaced to a first side of the base, the wheels for supporting the IV holder on a floor;
 a post, a first end of the post extending from a second side of the base opposite from the first side of the base, a distal second end area of the post having an IV bag hook, the post having an offset area between the first end and the second end such that the IV bag hook is positioned over a center of the base; and
 means for allowing rotation of an IV bag includes a bearing, a first rotating member of the bearing interfaced to the distal second end area of the post and a second rotating member of the bearing interfaced to the IV bag hook.

9. The IV holder of claim 8, wherein the offset area is a curved section of the post.

10. The IV holder of claim 9, wherein the curved section is parabolic.

11. The IV holder of claim 8, further comprising means for damping movement of an IV bag that hangs from the IV bag hook.

12. The IV holder of claim 11, wherein the means for damping comprises a pair of intertwined circular links, a first circular link of the pair of intertwined circular links interfaced to the distal second end area of the post and a second circular link of the pair of intertwined circular links interfaced to the IV bag hook.

13. The IV holder of claim 8, wherein the means for allowing rotation of the IV bag that hangs from the IV bag hook.

14. An IV holder comprising:
 a base, the base having a plurality of wheels interfaced to a first side of the base, the wheels for supporting the IV holder on a floor; and
 means for supporting an IV bag hook over a center of the base; and
 means for allowing rotation of the IV bag hook including a bearing, a first rotating member of the bearing interfaced to the means for supporting the IV bag hook and a second rotating member of the bearing interfaced to the IV bag hook.

15. The IV holder of claim 14, wherein the means for supporting comprises a post, a first end of the post extending from a second side of the base opposite from the first side of the base, the IV bag hook interfaced to a distal second end area of the post, the post having an offset area between the first end and the second end such that the IV bag hook is positioned over a center of the base.

16. The IV holder of claim 15, wherein the offset area is a curved section of the post.

17. The IV holder of claim 16, wherein the curved section is parabolic.

18. The IV holder of claim 15, wherein the offset area is a series of sections of the post, each of the series of sections of the post are at right angles to adjacent sections of the post.

* * * * *